US012668611B2

(12) United States Patent
Kim et al.

(10) Patent No.: US 12,668,611 B2
(45) Date of Patent: Jun. 30, 2026

(54) CELL-PENETRATING PEPTIDE AND USE THEREOF

(71) Applicant: IMNEWRUN, INC., Suwon-si (KR)

(72) Inventors: Han Joo Kim, Suwon-si (KR); Minah Suh, Suwon-si (KR); Yong Ho Kim, Suwon-si (KR); Jae Cheol Lee, Suwon-si (KR); Euna Lee, Suwon-si (KR); Ji Young Nam, Suwon-si (KR); Ho Jae Choi, Suwon-si (KR)

(73) Assignee: IMNEWRUN, INC., Suwon-si (KR)

( * ) Notice: Subject to any disclaimer, the term of this patent is extended or adjusted under 35 U.S.C. 154(b) by 847 days.

(21) Appl. No.: 17/918,471

(22) PCT Filed: Apr. 28, 2020

(86) PCT No.: PCT/KR2020/005557
§ 371 (c)(1),
(2) Date: Oct. 21, 2022

(87) PCT Pub. No.: WO2021/215568
PCT Pub. Date: Oct. 28, 2021

(65) Prior Publication Data
US 2023/0144488 A1     May 11, 2023

(30) Foreign Application Priority Data

Apr. 23, 2020     (KR) ........................ 10-2020-0049621

(51) Int. Cl.
| | |
|---|---|
| *C07K 7/08* | (2006.01) |
| *A61K 47/62* | (2017.01) |
| *C12N 9/22* | (2006.01) |

(52) U.S. Cl.
CPC ................ *C07K 7/08* (2013.01); *A61K 47/62* (2017.08); *C12N 9/22* (2013.01); *C07K 2319/60* (2013.01)

(58) Field of Classification Search
CPC .................................. C07K 7/08; A61K 47/62
See application file for complete search history.

(56) References Cited

U.S. PATENT DOCUMENTS

| | | | |
|---|---|---|---|
| 9,694,087 | B2 | 7/2017 | Shin et al. |
| 10,918,727 | B2 | 2/2021 | Lee et al. |
| 2010/0099626 | A2 | 4/2010 | Divita et al. |
| 2017/0081661 | A1 | 3/2017 | Divita et al. |
| 2018/0214565 | A1 | 8/2018 | Lee |

FOREIGN PATENT DOCUMENTS

| | | | | | |
|---|---|---|---|---|---|
| EP | 2784081 | A1 * | 10/2014 | .......... | A61K 31/192 |
| KR | 10-2007-0083218 | A | 8/2007 | | |
| KR | 10-2009-0016890 | A | 2/2009 | | |
| KR | 101258279 | * | 4/2013 | ............. | A61K 47/42 |
| KR | 101258279 | B1 | 4/2013 | | |
| KR | 10-1647804 | | 8/2016 | | |
| KR | 10-2017-0114997 | A | 10/2017 | | |
| WO | 2013077681 | A1 | 5/2013 | | |

OTHER PUBLICATIONS

Yi, H. et al. Development and Application of Cell-penetrating Peptides. Journal of Bacteriology and Virology. 2013, vol. 43, No. 3, pp. 177-185.
Int'l Search Report and Written Opinion issued Jan. 19, 2021 in Int'l Application No. PCT/KR2020/005557, translation of ISR only.
Elliott et al., Intercellular Trafficking and Protein Delivery by a Herpesvirus Structural Protein, 88 Cell 223-233 (Jan. 24, 1997).
Notice of Allowance issued in corresponding Chinese Patent Application 9-5-2021-027024734 on Apr. 4, 2021.
Extended European Search Report, issued May 24, 2024, in corresponding European Application No. 20932140.5-1111, 8 pages.

* cited by examiner

*Primary Examiner* — Amber D Steele
(74) *Attorney, Agent, or Firm* — PANITCH SCHWARZE BELISARIO & NADEL LLP

(57)     ABSTRACT

The present disclosure relates to novel cell penetrating peptides and uses thereof. Since 12 types of cell-penetrating peptides according to the present disclosure were confirmed to have excellent cell permeability and an excellent substance delivery effect in vitro and in vivo, the cell-penetrating peptides are expected to be useful in the field of research, and in the field of diagnosis or treatment of various diseases, by being capable of effectively delivering a substance with biological activity into the body, such as cells and tissues.

2 Claims, 12 Drawing Sheets

Specification includes a Sequence Listing.

CELL-PENETRATING PEPTIDE AND USE THEREOF

CROSS-REFERENCE TO RELATED APPLICATIONS

This application is a Section 371 of International Application No. PCT/KR2020/005557, filed Apr. 28, 2020, which was published in the Korean language on Oct. 28, 2021 under International Publication No. WO 2021/215568 A1, which claims priority under 35 U.S.C. § 119(b) to Korean Application No. 10-2020-0049621, filed Apr. 23, 2020, the disclosures of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "689942_1219US_Sequence_Listing", creation date of Oct. 21, 2022, and having a size of 3,210 bytes. The sequence listing submitted via EFS-Web is part of the specification and is herein incorporated by reference in its entirety.

TECHNICAL FIELD

The present disclosure relates to an intracellular delivery technology for delivering a biologically active substance into a cell, more specifically, a novel cell-penetrating peptide having excellent cell permeability and uses thereof.

BACKGROUND ART

To date, studies have been conducted on intracellular delivery and applications thereof, of various small-molecule compounds, and macromolecule substances such as proteins, peptides, RNA, DNA, and the like. In particular, attempts have been made to regulate intracellular functions through delivery of various proteins such as enzymes like SOD, catalases, and SOCS, inhibitory proteins of intracellular signaling proteins such as mutants of dnPI3K and ZAP70, transcription factor proteins such as Foxp3 and RORgt, or DNA binding domains of transcription factors. In addition, attempts have been made to control rejection that occurs during organ and cell transplantation by delivering small-molecule compound drugs such as cyclosporin A into cells and tissues, and to control autoimmunity such as psoriasis.

However, in general, substances that are hydrophilic or have large molecular weights cannot enter the cell due to a barrier called a cell membrane. The cell membrane prevents macromolecules such as peptides, proteins, and nucleic acids from entering the cell, and even when macromolecules enter the cell through a physiological mechanism called endocytosis by cell membrane receptors, the macromolecules are fused with the lysosomal compartment of the cell and eventually decompose. Therefore, there are many limitations in the treatment and prevention of diseases when using these macromolecules. In addition, in the case of anticancer drugs, it is necessary to overcome obstacles such as multidrug resistance in order to deliver the drugs into cells. Accordingly, in order to prevent drug degradation, many methods have been proposed to directly deliver various macromolecules and drug-containing carriers into cells without going through endocytosis. These methods include microinjection, electroporation, etc., which have the potential to damage the cell membrane. Other methods include a method of using a cell-penetrating material. However, even when drugs are delivered into cells through these methods, there is a problem in that the drugs must be moved to a specific organelle in order to exert a drug effect.

Therefore, various drug delivery systems capable of overcoming the above limitations and increasing stability and delivery efficiency of substances have been researched and developed, and representative examples include liposomes and micelles. Liposomes are artificially made phospholipid carriers capable of encapsulating both lipophilic and hydrophilic drugs, and since liposomes are biocompatible materials, they are non-toxic, and protect drugs from external environments. However, there are disadvantages of delayed absorption, limitation in distribution, lowered metabolic rates, and rapid removal from the blood by being captured by cells of the liver or spleen. Although micelles have characteristics that can increase solubility and bioavailability of drugs, many studies are still needed on effects related to movement of substances into cells and preclinical and clinical applicability. Due to these limitations, there is a need for new agents that may effectively deliver biomaterials into the body, have no cytotoxicity, and in particular, do not enter through endocytosis.

In this regard, cell-penetrating peptides have been attracting attention as a new alternative. A cell-penetrating peptide is a kind of signal peptide and is a peptide that is a combination of specific amino acid sequences used for the purpose of delivering macromolecular substances such as proteins, DNA, RNA, etc. into cells. For example, since the 1990s, when 11 amino acid sequences present in TAT proteins derived from HIV viruses were shown to enable delivery of beta-galactosidase (120 kDa) proteins into a cell or tissue, related research has been conducted in earnest. Antennapedia (Penetratin) derived from a Drosophila protein, VP22 derived from HSV-1 viruses (Elliott, G. et al., Cell, 88:223, 1997), and Pep-1 derived from large antigen T of simian virus 40 have been considered representative first-generation cell-penetrating peptides and have been widely used together with TAT. In addition, peptides in which several cationic amino acids such as arginine and lysine are repeatedly linked, such as poly-arginine and poly-lysine, have also been reported to have excellent cell permeability, and are being applied to various substance delivery methods. However, most of these cell-penetrating peptides have the potential for immunogenicity and toxicity, and are considered to have poor delivery efficacy into human cells. Therefore, it is necessary to develop a cell-penetrating peptide that does not cause toxicity, has safety in vivo, and is capable of effectively delivering substances.

DESCRIPTION OF EMBODIMENTS

Technical Problem

As a result of research efforts to develop a new cell-penetrating peptide peptide that may overcome the above limitations, the present inventors designed and synthesized a new peptide with better permeability than the cell-penetrating peptides in the art, and experimentally confirmed in vitro and in vivo that the amino acids at the 2nd and 6th positions in the peptide are important amino acids for determining cell permeability, and based on this, the present disclosure was completed.

Accordingly, an object of the present disclosure is to provide a novel cell-penetrating peptide.

Another object of the present disclosure is to provide a complex including the cell-penetrating peptide and a biologically active substance.

In addition, another object of the present disclosure is to provide a composition for substance delivery including the complex, and a substance delivery method including treating cells with the composition.

However, technical problems to be solved by the present disclosure is not limited to the above-mentioned problems, and still other problems not mentioned will be clearly understood by those skilled in the art from the following description.

Solution to Problem

In order to achieve the object of the present disclosure as described above, the present disclosure provides a cell-penetrating peptide consisting of an amino acid represented by General Formula 1:

$$X_1\text{-}X_2\text{-} \ldots X_{n-1}\text{-}X_n, \qquad \text{General Formula 1}$$

wherein in General Formula 1, $n \geq 16$, $X_2$ is His (H), $X_6$ is Leu (L), and amino acids other than $X_2$ and $X_6$ are any one selected from the group consisting of Gly (G), His (H), Glu (E), Arg (R), Lys (K), Ser (S), Asp (D), Trp (W), Val (V), Thr (T), Ala (A), Asn (N) and Tyr (Y).

In an embodiment of the present disclosure, n in General Formula 1 may be 16.

In another embodiment of the present disclosure, the cell-penetrating peptide may consist of any one amino acid sequence selected from the group consisting of SEQ ID NOS: 1 to 12.

In still another embodiment of the present disclosure, the cells may be selected from the group consisting of brain endothelial cells, cancer cells, blood cells, lymphocytes, immune cells, stem cells, induced pluripotent stem cells (iPSCs), neural stem cells (NSCs), T cells, B cells, natural killer cells (NK cells), macrophages, microglia, neurons, astrocytes and muscle cells.

In addition, the present disclosure provides a complex including the cell-penetrating peptide and a biologically active substance.

In an embodiment of the present disclosure, the biologically active substance may be at least one selected from the group consisting of chemical compounds, proteins, glycoproteins, peptides, antibodies, enzymes, nucleases, hormones, cytokines, transcription factors, toxins, nucleic acid, carbohydrate, lipids, glycolipids, natural products, semisynthetic drugs, drugs, microparticles, nanoparticles, liposomes, viruses, quantum dots, and fluorochromes.

In another embodiment of the present disclosure, the nuclease may be selected from the group consisting of CRISPR associated protein 9 (CAS9), CAS12, CAS13, CAS14, CAS variants, CxxC-finger protein-1 (Cfp1), zinc-finger nucleases (ZEN), and transcription activator-like effector nucleases (TALEN).

In another embodiment of the present disclosure, the nucleic acid may be selected from the group consisting of DNA, RNA, antisense oligonucleotide (ASO), microRNA (miRNA), small interfering RNA (siRNA), aptamer, locked nucleic acid (LNA), peptide nucleic acid (PNA), and morpholino.

In addition, the present disclosure provides a composition for substance delivery including the complex.

In addition, the present disclosure provides a substance delivery method including treating cells with the composition.

Advantageous Effects of Disclosure

In the present disclosure, a novel cell-penetrating peptide was synthesized, and excellent cell permeability and substance delivery effect thereof were experimentally confirmed in vitro and in vivo. Therefore, the cell-penetrating peptide according to the present disclosure is capable of effectively delivering a biologically active substance into a living body, such as cells and tissues, and is expected to be useful in the field of research, and in the field of diagnosis or treatment of various diseases.

BEST MODE

Figure 1:
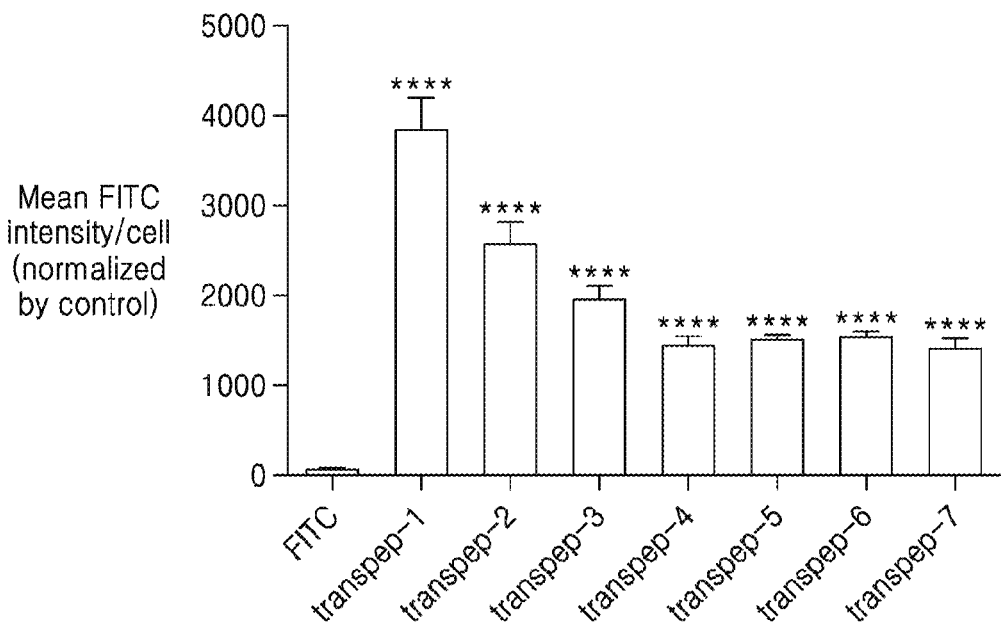
FIG. 1 shows results for verifying cell permeability in vitro after treating cells with a substance, in which fluorescein isothiocyanate (FITC) is linked to 12 synthesized peptides, at a concentration of 4 μM.
Figure 1:
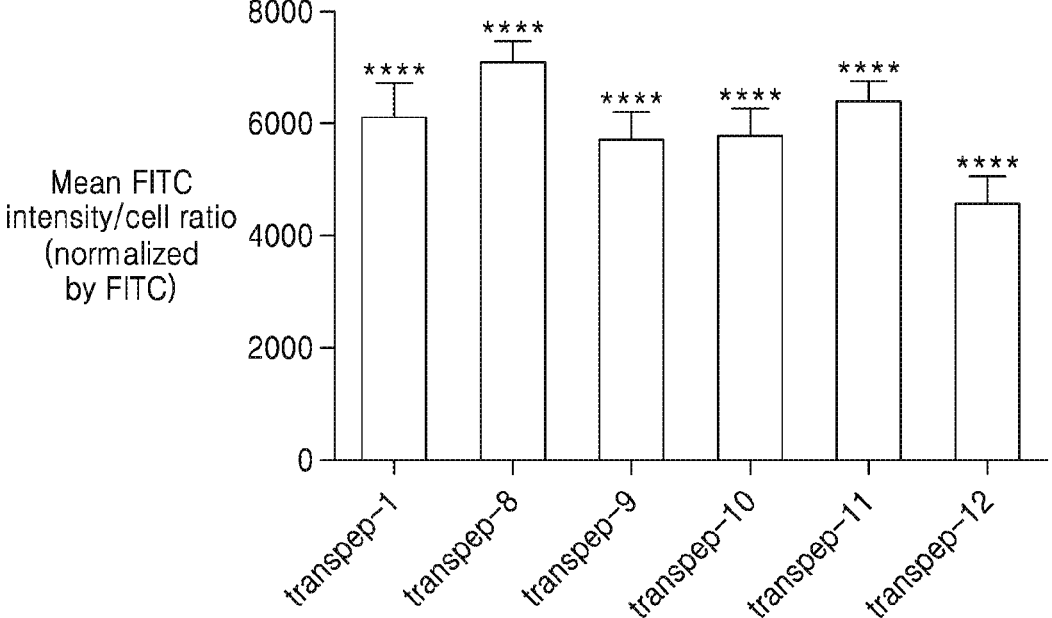

The present disclosure relates to a cell-penetrating peptide that may be useful in the field of research, and in the field of diagnosis or treatment of various diseases, and relates to a basic platform peptide structure that may be extended to an unlimited number of designs.

Hereinafter, the present disclosure will be described in detail.

The present disclosure provides a cell-penetrating peptide consisting of amino acids represented by the following General Formula I:

$$X_1\text{-}X_2\text{-} \ldots X_{n\text{-}1}\text{-}X_n,$$ General Formula 1 wherein in General Formula 1, $n \geq 16$, $X_2$ is His (H), $X_6$ is Leu (L), and amino acids other than $X_2$ and $X_6$ are any one selected from the group consisting of Gly (G), His (H), Glu (E), Arg (R), Lys (K), Ser (S), Asp (D), Trp (W), Val (V), Thr (T), Ala (A), Asn (N) and Tyr (Y).

"Cell penetrating", used herein, refers to an ability or property of a peptide to penetrate a cell (membrane) and permeate into the cell.

"Peptide", used herein, is a polymer of amino acids. Usually, a form in which a few amino acids are linked is called a peptide, and when many amino acids are linked, the same is called a protein. In such peptide and protein structures, the linkages between amino acids are formed by an amide bond or a peptide bond. A peptide bond is a bond between a carboxyl group (—COOH) and an amino group (—NH$_2$), in which water (H$_2$O) is removed and —CO—NH— is formed.

In the present disclosure, the cell-penetrating peptide represented by General Formula 1 includes a sequence of 1 to 16 continuous amino acids having His (H) at the 2nd position and Leu (L) at the 6th position, from the N-terminus, and may further include various amino acids at the C-terminus that may increase its efficiency as a cell-penetrating peptide.

More specifically, the cell-penetrating peptide according to the present disclosure may consist of any one amino acid sequence selected from the group consisting of SEQ ID NOS: 1 to 12, but is not limited thereto. In this regard, the cell-penetrating peptide may include an amino acid sequence having sequence homology of 70% or more, preferably 80% or more, more preferably 90% or more, most preferably 91% or more, 92% or more, 93% or more, 94% or more, 95% or more, 96% or more, 97% or more, 98% or more, or 99% or more, with the amino acid sequence represented by SEQ ID NOS: 1 to 12.

In the present disclosure, the cell type permeable to the cell-penetrating peptide includes, but is not limited to, any one selected from the group consisting of brain endothelial cells, cancer cells, blood cells, lymphocytes, immune cells, stem cells, induced pluripotent stem cells (iPSC), neural stem cells (NSC), T cells, B cells, natural killer cells (NK cells), macrophages, microglia, neurons, astrocytes, and muscle cells.

The peptide of the present disclosure may be manufactured so that the purity of each peptide is 90% or more through a peptide synthesis method or a manufacturing method known to those skilled in the art, for example, may be directly synthesized, or purchased and used after requesting production from a peptide manufacturer. The peptide may be manufactured through a peptide synthesis method or a manufacturing method known to those skilled in the art to a D-form or an L-form, a peptide in which only a part of the sequence is formed as a D-form or an L-form, or to a racemate form thereof. In addition, in order to increase stability of the peptide, other modifications known in the art are possible. In the present disclosure, peptides were preferably synthesized by using a solid state peptide synthesis method, but as described above, the peptide synthesis method and conditions are not limited thereto.

The present inventors designed and synthesized cell-penetrating peptides having various sequences and lengths based on previous studies on sequential and structural analysis of artificial cell-penetrating peptides or human-derived cell-penetrating domains known in the art. As a result, a cell-penetrating peptide consisting of an amino acid sequence of SEQ ID NO: 1 showing excellent cell permeability and an excellent substance delivery effect was discovered, and the cell-penetrating peptide was named "transpep-1".

In addition, based on the three-dimensional structure of the transpep-1 peptide, it was expected that the amino acids at the 2nd and 6th positions in the amino acid sequence of SEQ ID NO: 1 would have an important effect on cell permeability.

Based on this hypothesis, the present inventors confirmed the hypothesis by synthesizing various peptides, in which the amino acids at the 2nd and/or 6th positions are substituted, or amino acids at other positions are substituted, and comparing cell permeability thereof.

More specifically, in an example of the present disclosure, as a result of synthesizing 12 cell-penetrating peptides and then verifying cell permeability thereof in vitro, it was confirmed that all 12 cell-penetrating peptides satisfying the platform peptide structure according to the present disclosure exhibit excellent cell permeability (see Example 2).

In another example of the present disclosure, an in vitro cell permeability analysis was performed after synthesizing single or double mutation peptides, in which amino acids at the 2nd and/or 6th positions from the N-terminus are substituted. As a result, it was confirmed that when only one of amino acids at the 2nd and 6th positions are substituted or both of the amino acids are substituted, cell permeability of the peptide is significantly reduced, and therefore, it was specifically demonstrated that the amino acids at the two positions are important for function of the cell-penetrating peptide according to the present disclosure (see Example 3).

In another example of the present disclosure, in order to verify in vivo cell permeability and substance delivery effects of the 12 peptides according to the present disclosure, cell-penetrating peptide-GFP was prepared by binding GFP, a fluorescent protein, as a carrier to a representative peptide having an amino acid sequence of SEQ ID NO: 1. Furthermore, GFP, a negative control, and cell-penetrating peptide-GFP were each injected into mice through the tail vein, and after 24 hours, brains were extracted from the mice to prepare cerebral cortex and hippocampal tissue sections. As a result of performing immunohistochemistry (IHC) using the fragment and analyzing the fluorescence images and their quantitative results, it was confirmed that the cell-penetrating peptide according to the present disclosure has excellent cell permeability even in vivo and is capable of effectively delivering a substance into cells as a carrier (See Example 5).

In another example of the present disclosure, it was attempted to compare cell permeability of a cell-penetrating peptide known in the art and the peptides according to the present disclosure. To this end, angiopep-2-fluorescein-5-isothiocyanate (FITC) was prepared by using angiopep-2, a known cell-penetrating peptide, and experiments for an in vitro cell permeability analysis and in vivo BBB permeability analysis were each performed by using the above-prepared transpep-1-FITC. As a result, the cell-penetrating peptide according to the present disclosure was shown to have significantly higher cell permeability compared to angiopep-2 and excellent in vivo stability and delivery efficiency (see Example 6).

From the results of the example, it may be seen that the peptide according to the present disclosure may be used as a carrier capable of introducing an arbitrary substance bound to the peptide into a cell.

Accordingly, as another aspect of the present disclosure, the present disclosure provides a complex including the cell-penetrating peptide and a biologically active substance.

In the present disclosure, the complex includes all of: those in which the peptide and the substance are simply mixed, those formed by mixing the peptide and the substance, or those generated by connection or conjugation of the peptide and the substance by a chemical bond. In addition, the complex may be connected by a physical bond, a chemical bond, a covalent bond, a non-covalent bond, self-assembly, or may be connected in an integrated or fused form by using a mediator.

In addition, the complex may be a complex formed by expressing the peptide and the biologically active material in a fused state. For example, when a gene expressing the peptide and a biologically active material is inserted into one vector, and an organism is transformed with the vector to express the gene inserted into the vector, the peptide and the biologically active material may be expressed as fusion proteins. When expressed as a fusion protein, any linker may be included between the peptide and the biologically active material.

In addition, in the complex according to the present disclosure, the cell-penetrating peptide may include forms in which single or plural units are combined, in order to efficiently deliver a biologically active substance into a cell, and a number of combinations of the cell-penetrating peptides may be easily selected or adjusted by those skilled in the art, depending on the biologically active substance to be delivered.

In the present disclosure, a biologically active substance capable of forming a complex by binding to a cell-penetrating peptide preferably refers to "a substance having biological or pharmaceutical activity", and refers to one that may be penetrated into cells (into the cytoplasm or the nucleus) to participate in the regulation of physiological activity or to express pharmacological effects, or a substance having biological activity in various parts of the body, such as cells, tissues, cellular matrix, and blood, to which the substance must be transported and act. For example, the biologically active substance may be at least one selected from the group consisting of chemical compounds, proteins, glycoproteins, peptides, antibodies, enzymes, nucleases, hormones, cytokines, transcription factors, toxins, nucleic acid, carbohydrate, lipids, glycolipids, natural products, semi-synthetic drugs, drugs, microparticles, nanoparticles, liposomes, viruses, quantum dots and fluorochromes, but is not limited thereto.

The nuclease may be one selected from the group consisting of CRISPR associated protein 9 (CAS9), CAS12, CAS13, CAS14, CAS variants, CxxC-finger protein-1 (Cfp1), zinc-finger nucleases (ZEN) and transcription activator-like effector nuclease (TALEN), but is not limited thereto.

The nucleic acid may be selected from the group consisting of DNA, RNA, antisense oligonucleotide (ASO), microRNA (miRNA), small interfering RNA (siRNA), aptamer, locked nucleic acid (LNA), peptide nucleic acid (PNA), and morpholino, and may further include decoy DNA, plasmid, shRNA, antisense RNA, oligoribonucleotide, or transfer RNA, but is not limited thereto.

The drug may be selected from the group consisting of chemical drugs, bio-drugs, nucleic acid drugs, peptide drugs, protein drugs, natural product drugs, hormones, contrast agents, and antibodies, but is not limited thereto.

The "bio-drug" refers to various biopharmaceuticals such as (original) biologics, biogenerics, biobetters, and biosuperiors. The bio-drug means any drug manufactured, secreted, or semi-synthesized from a biological origin, and includes, but is not limited to, vaccines, blood products, antigens, cell preparations, gene therapy products, stem cells, and the like.

The nanoparticle may be selected from the group consisting of iron oxide, gold, carbon nanotubes, and magnetic beads, but is not limited thereto.

In another aspect of the present disclosure, the present disclosure provides a composition for substance delivery including the complex as an active ingredient.

The composition for substance delivery may be used to deliver a biologically active material to a living tissue or blood or to promote cell permeation. The composition may be delivered through cells constituting a living tissue or through cell-to-cell junctions, but there is no limitation in the delivery method.

The living tissue refers to at least one selected from epithelial tissue, muscle tissue, nervous tissue, and connective tissue, and since each organ may consist of one or more tissues, various living organs such as mucosa, skin, brain, lung, liver, kidney, spleen, heart, stomach, large intestine, digestive tract, bladder, ureter, urethra, ovary, testis, genitalia, muscle, blood, blood vessels, lymphatic vessels, lymph nodes, thymus, pancreas, adrenal gland, thyroid gland, parathyroid gland, larynx, tonsils, bronchi, and alveoli may be included, but the living tissue is not limited thereto.

When attempting to deliver the complex to a specific cell, tissue or organ, the biologically active substance may form a complex by binding to an extracellular protein of a ligand that may bind selectively to a receptor specifically expressed in a specific cell, tissue or organ, or a monoclonal antibody (mAb) that may bind specifically to these receptors or ligands, and modified forms thereof. The binding between the peptide and the biologically active substance is either by indirect linking by cloning technique using an expression vector at a nucleotide level, or by direct linking by chemical or physical covalent or non-covalent bonding between the peptide and the biologically active substance.

In the present disclosure, when the composition including the complex is used as a pharmaceutical composition, the composition may include the active ingredient in an amount of 0.0001 wt % to 50 wt % based on the total weight of the composition.

The composition of the present disclosure may contain one or more active ingredients exhibiting the same or similar function in addition to the active ingredient.

The composition of the present disclosure may be prepared by including one or more pharmaceutically acceptable carriers for administration, in addition to the active ingredients described above. The pharmaceutically acceptable carrier may be used by mixing with at least one of saline, sterile water, Ringer's solution, buffered saline, dextrose solution, maltodextrin solution, glycerol, ethanol, liposome, and a mixture thereof, and an antioxidant, a buffer, a bacteriostat, and other additives in the art may be added, as needed. In addition, diluents, dispersants, surfactants, binders and lubricants may be additionally added to formulate injectable formulations such as aqueous solutions, suspensions, emulsions, pills, capsules, granules or tablets, and antibodies specific to a target organ or other ligands may be used by binding to the carrier, in order that the composition may act specifically on the target organ. Furthermore, the composition may be preferably formulated according to each disease or component using an appropriate method in the art or a method disclosed in Remington's literature.

The composition including the complex as an active ingredient may be delivered in vivo by injecting through a route, such as an intravenous, an intraperitoneal, an intramuscular, an intrathecal, an intracerebroventricular, a subcutaneous, an intradermal, a nasal, a mucosal, an inhalation. and oral route. A dose have a wide range according to the subject's weight, age, sex, health, diet, administration time, administration manner, excretion rate, and severity of the disease.

As another aspect of the present disclosure, the present disclosure provides a substance delivery method including treating the cells with the composition for substance delivery.

Since the cell-penetrating peptide having a function of substance delivery according to the present disclosure is a very small peptide, it is possible to minimize any biological interference with the active material that may occur.

Hereinafter, preferred examples are presented to help understanding of the present disclosure. However, the following examples are only provided for easier understanding of the present disclosure, and the contents of the present disclosure are not limited by the following examples.

EXAMPLES

Example 1. Preparation of Cell-Penetrating Peptide Candidates 1-1. Design of Cell-Penetrating Peptide Candidates The present inventors designed and synthesized cell-penetrating peptides having various sequences and lengths based on the analysis results of several cell-penetrating peptides in the art in previous studies, and verified cell permeability thereof. As a result, a cell-penetrating peptide consisting of an amino acid sequence of SEQ ID NO: 1 showing the most excellent cell permeability was discovered, and the cell-penetrating peptide was named "transpep-1".

Furthermore, the present inventors synthesized 11 peptide variants in which one or two amino acids were substituted in the transpep-1 sequence in order to additionally discover cell-penetrating peptides. In this regard, based on the three-dimensional structure of the transpep-1 peptide, the 2nd and 6th amino acids were expected to affect cell permeability, and candidates of cell-penetrating peptides were synthesized by retaining the amino acids of the two positions while modifying amino acids of other positions. Overall, a total of 12 peptides synthesized in the present disclosure and their sequences are shown in Table 1 below.

TABLE 1

| No. | Substance | Sequence | SEQ ID NO |
|---|---|---|---|
| 1 | transpep-1 | GHHERLKSDEWSVTSG | 1 |
| 2 | transpep-2 | GHHERLKSAEWSVTSG | 2 |
| 3 | transpep-3 | GHHERLKSDAWSVTSG | 3 |
| 4 | transpep-4 | GHHERLKSDEWAVTSG | 4 |
| 5 | transpep-5 | GHHERLKSAAWSVTSG | 5 |
| 6 | transpep-6 | GHHERLKSAEWAVTSG | 6 |
| 7 | transpep-7 | GHHERLKSDAWAVTSG | 7 |
| 8 | transpep-8 | GHHERLKSEEWSVTSG | 8 |
| 9 | transpep-9 | GHHERLKSYEWSVTSG | 9 |
| 10 | transpep-10 | GHHERLKSDDWSVTSG | 10 |
| 11 | transpep-11 | GHHERLKSDYWSVTSG | 11 |
| 12 | transpep-12 | GHHERLKSDEWNVTSG | 12 |

1-2. Synthesis, Separation and Purification of Peptide Candidates

The present inventors used a solid state peptide synthesis (SSPS) method to synthesize each of the peptides described in Example 1-1. The method is an organic synthesis method in which a C-terminus of an amino acid, whose N-terminus is protected with F-moc, is joined to an N-terminus of the resin one by one. N, N-dimethylformamide (DMF) was used as a solvent for all reactions, and coupling of amino acids was proceeded by mixing an amino acid solution at a concentration of 2 M with 1 ml of 0.5 M N, N'-diisopropylcarbodiimide (DIC) and 0.5 ml of 1 M ethyl cyano (hydroxyimino)acetate (Oxyma), and reacting the same in a microwave synthesizer. In addition, amino acids were prepared by varying the reaction time, temperature, or microwave voltage for each amino acid sequence. In this regard, in order to synthesize the next amino acid, the F-moc of the previous amino acid has to be removed, and therefore, the F-moc protecting group was deprotected twice at 80° C. for 2 minutes, by using 80% DMF and 20% piperidine solutions. Between all the couplings and deprotectings, a process of alternately washing with DMF and methylene chloride (DCM) was performed three times each.

For the peptide synthesized through the above method, a fluorescent material including a carboxyl group (—COOH) at the N-terminus of the peptide may be linked by a chemical bonding method, in order to later observe and quantify cell permeability. In this regard, the fluorescent material that may be used includes fluorescein-5-isothiocyanate (FITC), cyanine 3 carboxylic acid, cyanine 5 carboxylic acid, cyanine 7 carboxylic acid, and the like. Specifically, among the fluorescent materials described above, in this example, FITC was attempted to be linked to the synthesized peptide. To this end, first, the last amino acid of the peptide synthesized in the solid resin was synthesized, and then FITC:DIC: Oxyma:resin were mixed well in a ratio of 2:2.5:4:1, and then the reaction in the resin was carried out at room temperature for 2 hours, by using a magnetic stirrer. Next, when the color of the resin changed from yellow to dark yellow or orange during the synthesis process, a process of alternately washing with DMF and methylene chloride was performed three times each. Subsequently, in order to separate the peptide/FITC from the solid resin, the synthesized resin was reacted for 2 hours using a stirrer in a cleavage solution in which trifluoroacetic acid (TFA):triisopropylsilane (TIS):distilled water were mixed at 95:2.5:2, and then the resin was filtered out with an asbestos filter. From the filtered solution, the solution was evaporated under nitrogen gas, and when a precipitate was formed, the precipitate was precipitated with diethyl ether stored cold. The precipitated peptide/FITC was dried in a vacuum and then dissolved in distilled water and lysophilized.

The lysophilized peptide was dissolved in distilled water or acetonitrile (ACN), and separated and purified by using reverse phase high-performance liquid chromatography. In this regard, solvent A (distilled water 99.9% and TFA 0.1%) and solvent B (distilled water 9.9%, acetonitrile 90%, and TFA 0.1%) were used as mobile phase solvents of the HPLC. The HPLC mobile phase started with 90% of Solvent A and 10% of Solvent B, and the separation proceeded while increasing the solvent B by 1%/min gradient. Thereafter, the separated peptide solution was lysophilized to remove the solvent and then dissolved in a desired solvent to conduct the experiment.

Example 2. In Vitro Cell Permeability Analysis

The present inventors performed in vitro cell permeability analysis on a total of 12 candidate peptides synthesized in Example 1 above. Specifically, hCMEC/D3 cells, which are human blood-brain barrier cells, were seeded in a 96-well plate at 18,000 cells/well, and incubated overnight at 37° C. under $CO_2$ conditions in a endothelial cell growth medium (EGM), which is an epithelial cell growth medium, until the cells reached 80% to 90% of the plate area. Subsequently, the 12 candidate peptides linked to FITC prepared in Example 1-2 and FITC alone, a negative control, were diluted in the medium to 4 μM to prepare an amount to be treated by 100 μl per well. Subsequently, the culture solution was removed from the cell culture plate by suction, and the peptide was diluted and treated with the solution prepared in advance, and then cultured at 37° C. under $CO_2$ conditions for 2 hours. Next, all the peptide-treated solutions were removed from each well by soaking, 100 μl of EGM was added, the plate was tapped 5 to 6 times, and a process of removal by suction was repeated twice. Thereafter, 100 μl of Hoechst 33342 was diluted in EGM at 1:5000, added to each well, and incubated at 37° C. under $CO_2$ conditions for 30 minutes. After incubation, DAPI and GFP fluorescence were image read by using a Cytation 5 equipment, and the cell nucleus was parcellated with DAPI by image processing. Subsequently, a value of 20 μM of FITC around the cell nucleus was measured, divided by DAPI to obtain a mean-FITC value, and the value was corrected with a value of FITC experimental group, a negative control group, to calculate permeability in the blood-brain barrier cells.

As a result, as shown in FIG. 1, it was confirmed with FITC fluorescence that all of the 12 peptides had cell permeability, when each of the peptides linked to FITC was treated at a concentration of 4 μM.

Example 3. Verification of Positions of Amino Acids Important for Cell Permeability As described above in Example 1, the present inventors predicted that the 2nd (AA2) and 6th (AA6) amino acid residues in the transpep-1 cell-penetrating peptide would have an important effect on cell permeability, and performed the following experiment for verification.

To this end, first, a single mutation peptide, in which histidine (H), which is the second amino acid of the transpep-1 peptide, or leucine (L), which is the sixth amino acid of the transpep-1 peptide, is respectively substituted with alanine (A), or arginine (R) was synthesized, and cell permeability was analyzed in the same manner as in Example 2.

TABLE 2

| No. | Substance | Mutation |
|---|---|---|
| 1 | #1 | AA2 H->A |
| 2 | #2 | AA6 L->A |
| 3 | #3 | AA2 H->R |
| 4 | #4 | AA6 L->V |

Figure 2A:
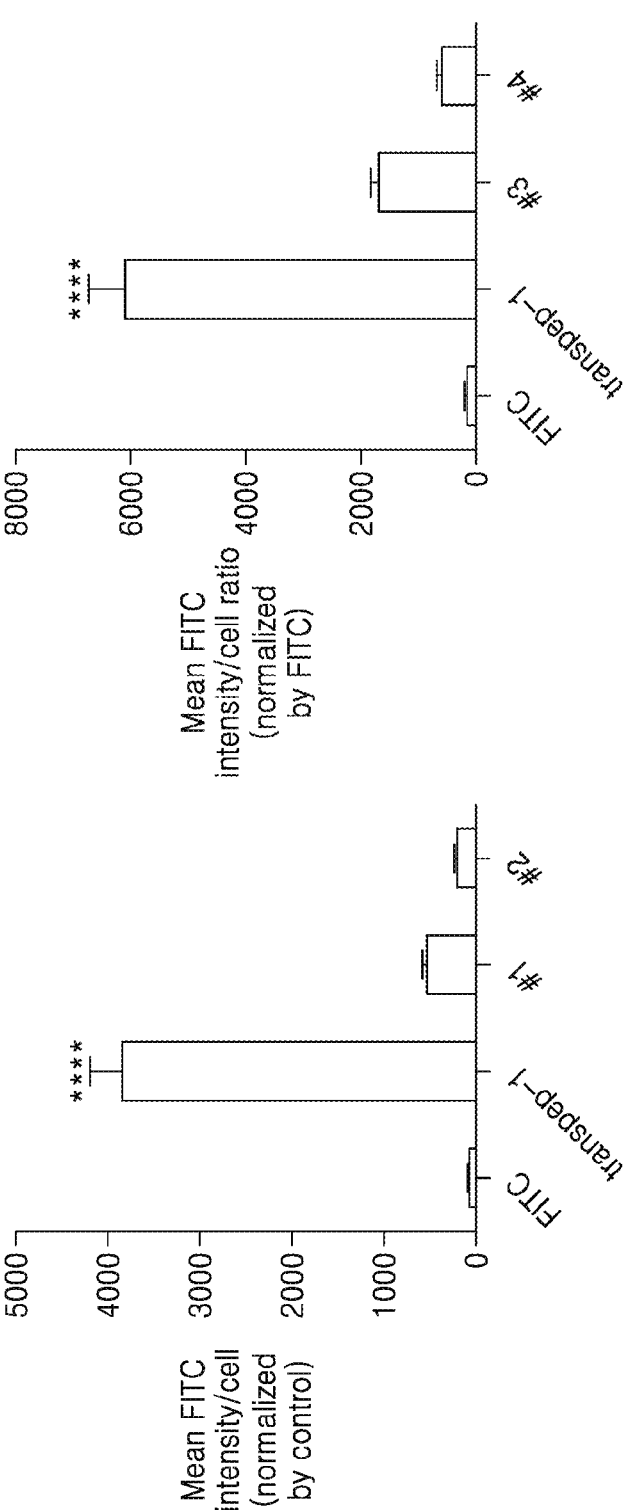
FIG. 2A shows results of conducting an in vitro cell permeability analysis using mutant peptides with single mutations in the amino acids of the two positions as shown in Table 2, in order to analyze effects of the second and sixth amino acids on cell permeability in the cell-penetrating peptide according to the present disclosure.

As a result, as shown in FIG. 2A, in the case of four mutant peptides, in which the 2nd or 6th amino acid residue was mutated, cell permeability was confirmed to be significantly reduced, compared with transpep-1, which was confirmed to have cell permeability in Example 2.

Furthermore, in order to further confirm the importance of the two amino acid residues, a peptide in which all of the 2nd and 6th amino acids are substituted with alanine was synthesized as shown in Table 3 below, and in addition, mutant peptides were synthesized, in which a double mutation is induced by substituting both the 2nd or the 6th amino acid and another amino acid with alanine in peptides No. 2, 3, and 4 of Table 1, synthesized in Example 1, in which permeability was confirmed, and the same experiment was performed as described above.

TABLE 3

| No. | Substance | Mutation |
|---|---|---|
| 1 | #5 | AA2 H->A/AA6 L->A |
| 2 | #6 | AA2 H->A/AA9 D->A |
| 3 | #7 | AA2 H->A/AA10 E->A |
| 4 | #8 | AA2 H->A/AA12 S->A |
| 5 | #9 | AA6 L->A/AA9 D->A |
| 6 | #10 | AA6 L->A/AA10 E->A |
| 7 | #11 | AA6 L->A/AA12 S->A |

Figure 2B:
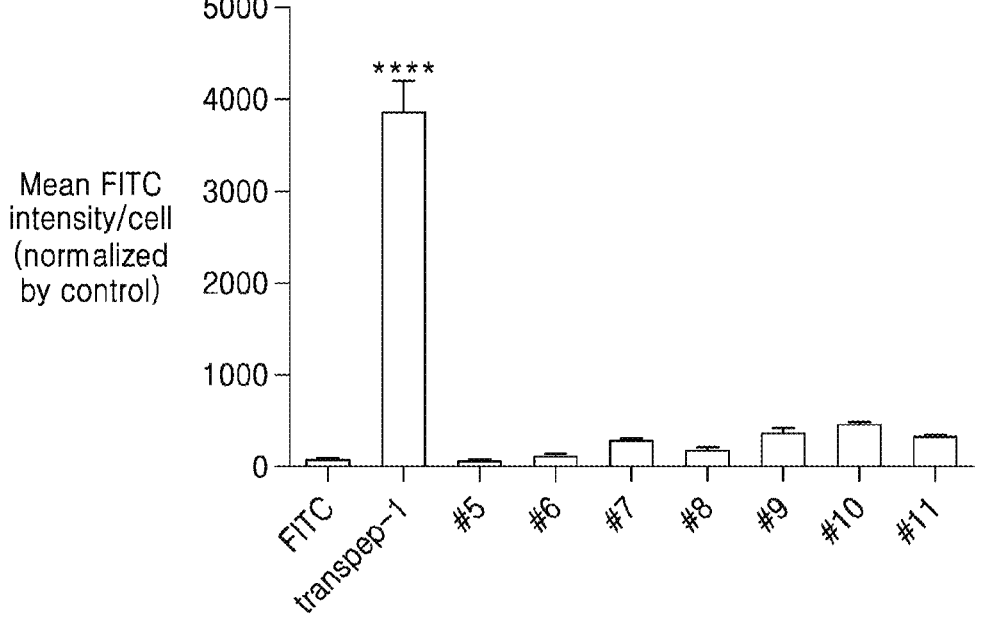
FIG. 2B shows results of conducting an in vitro cell permeability analysis using mutant peptides with double mutations in the amino acids including the amino acids of the two positions as shown in Table 3, in order to analyze effects of the second and sixth amino acids on cell permeability in the cell-penetrating peptide according to the present disclosure.

As a result, as may be seen in FIG. 2B, it was found that cell permeability was significantly reduced in all seven mutant peptides, in which a double mutation was induced. Through these results, it was found that histidine at the 2nd position and leucine at the 6th position in the cell-penetrating peptide of the present disclosure are important residues for determining cell permeability.

Example 4. Preparation of Cell-Penetrating Peptide Bound to GFP, a Fluorescent Protein In order to perform imaging of the delivery of the cell-penetrating peptide according to the present disclosure to tissue in the body in an in vivo cell permeability analysis and to verify function of the cell-penetrating peptide as a cargo carrier, the present inventors attempted to prepare a cell-penetrating peptide-GFP by binding a green fluorescence protein (GFP), which is a fluorescent protein, to the cell-penetrating peptide of the present disclosure. GFP is a representative fluorescent protein, has a size of 27 kDa, excitation peaks at 395 nm and 475 nm, and an emission peak at 509 nm.

Specifically, to prepare the cell-penetrating peptide-GFP, a transpep-1 peptide sequence of SEQ ID NO: 1 was inserted to the C-terminus of GFP by using a polynucleotide enzyme, and using the generated sequence as a template, a primer capable of binding to the N-terminus and the C-terminus was designed. The primer was amplified by PCR and then inserted into pET28a expression vectors to prepare recombinant expression vectors of the cell-penetrating peptide-GFP protein. After transforming *E. coli* BL21 (DE3) with the recombinant expression vector, *E. coli* was cultured until the O.D. value reached 0.5, and then IPTG was added at a concentration of 1 mM to induce expression of cell-penetrating peptide-GFP protein. Thereafter, SDS-PAGE was performed to confirm an expression level of the protein, and the protein was isolated and purified by using His-tag affinity chromatography.

Example 5. In Vivo Cell Permeability Analysis

The present inventors tried to verify in vivo cell permeability of the cell-permeable peptide according to the present disclosure.

For this purpose, the following experiment was performed using transpep-1 as a representative among the 12 peptides. Specifically, the cell-penetrating peptide-GFP prepared by the method described in Example 4 or negative control GFP was diluted in PBS to a concentration of 500 μM, and an amount of 100 μl was intravenously injected (i.v. injection) through the tail vein of C57BL/6 mice. After 24 hours, zoletyl was injected intraperitoneally (i.p. injection) at a dose of 0.625 ml/kg to anesthetize the mouse, and then a toe-pinch test was performed to confirm complete anesthesia. Next, 30 ml of physiological saline was perfused at a rate of 3 ml/min through atrial perfusion to remove blood from the body, and 30 ml of 4% paraformaldehyde solution was perfused at a rate of 3 ml/min to fix the tissue. After the brain was extracted from the skull of a fixed mouse, post-fixation was performed for 24 hours in a 4% paraformaldehyde solution at 4° C. Then, in order to prevent damage to cells during sectioning of the prepared tissue, the brain tissue was transferred to a 30% sucrose solution and the solution in the tissue was substituted for 48 hours at 4° C. After removing the sucrose solution remaining in the brain tissue, the tissue was rapidly frozen by using an optimal cutting temperature compound, and then a 50 μm tissue section was prepared by using a cryomicrotome.

In order to perform immunohistochemistry (IHC) on GFP proteins using the tissue section prepared by the above method, the tissue section was first immersed in a 100% methanol solution at 4° C. for 10 minutes, and then washed with PBS for 5 minutes, and the washing was repeated twice. After the washing, the tissue was covered with a blocking solution (CAS blocking solution), incubated at room temperature for 1 hour, and then the blocking solution was removed. Next, in order to induce an antibody response, the prepared tissue was covered with rabbit anti-GFP, which is primary antibodies diluted to 1:200 in PBS, and incubated at 4° C. for 24 hours, and washed with PBS for 5 minutes, and the washing was repeated three times, and then the tissue where the first response was completed was covered with goat anti-rabbit IgG/Alexa 488, which is secondary antibodies diluted to 1:200 in PBS, and incubated for 2 hours at room temperature, and washed with PBS for 5 minutes, and the washing was repeated twice.

On the other hand, in order to stain the cell nucleus, the tissue was covered with a DAPI solution diluted to 1:400 in PBS, incubated at room temperature for 10 minutes, and then washed with PBS for 5 minutes, and the washing was repeated twice. After the immunohistochemical staining experiment was completed, the tissue was sealed with a mounting solution, covered with a cover glass, and the circumference of the cover glass was sealed with nail polish and dried for 30 minutes. Delivered GFP and cell nuclei in the brain tissue mounted on the cover glass were imaged by using a confocal microscope, and the image of the tissue for analysis was acquired by using a 20× magnification lens in a range that the cerebral cortex and the hippocampus may be included. In addition, the images acquired by using a confocal microscope were taken at a resolution of 0.38 μm×0.38 μm×2.99 μm (width×height×depth) in a field of view (FOV) of 2.5 mm×2.5 mm×40 μm. For quantification of the acquired image, pre-processing processes were performed by cropping the lost part of the image in the range of FOV, and increasing the signal-to-noise ratio (SNR) by using a Gaussian filter. In order to quantify GFP in the cerebral cortex and hippocampal regions by using the preprocessed image, the cortex region and the hippocampal region were divided and parcellated based on the DAPI-stained cell nucleus to produce an atlas of the cortex and hippocampal regions within the tissue, and then, fluorescence intensity of GFP was measured to indicate a degree of immune response (immunoreactivity).

Figure 3A:
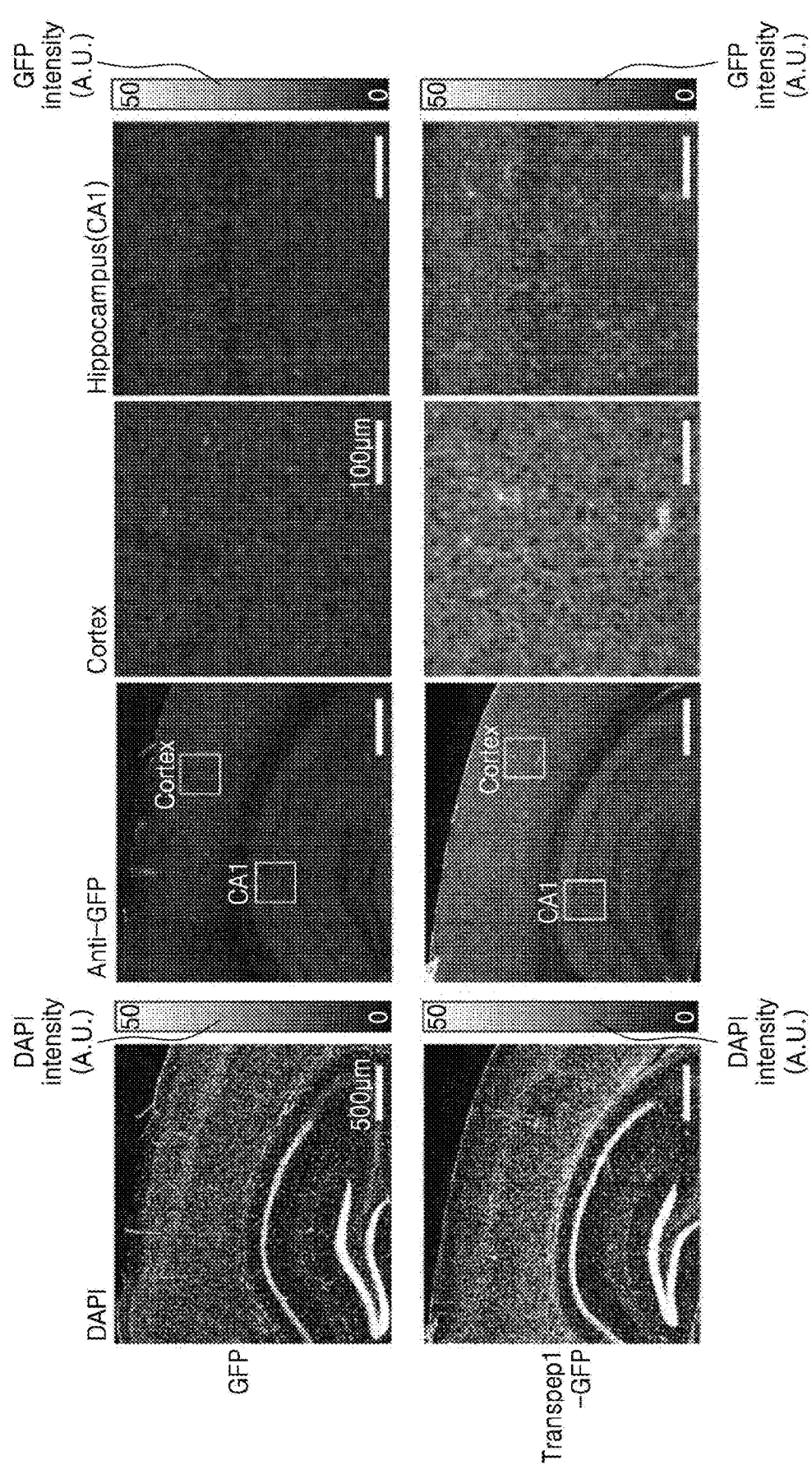
FIG. 3A shows in vivo fluorescence images for analyzing permeability into the cerebral cortex and hippocampal tissue of a mouse and a substance delivery effect, after preparing a peptide fusion by binding green fluorescent proteins (GFPs) to representative peptides of SEQ ID NO: 1 among the cell-penetrating peptides of the present disclosure.
Figure 3B:
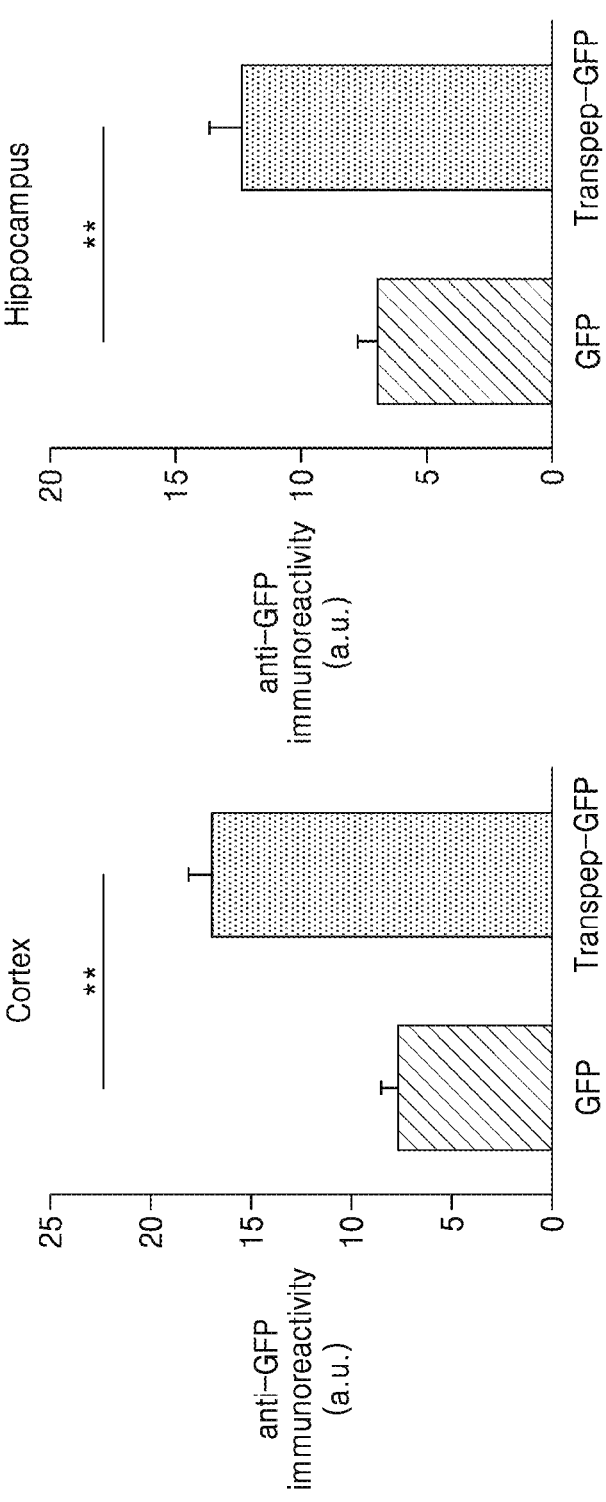
FIG. 3B shows quantitative results for the fluorescence images of FIG. 3A.

As a result of the experiment, as may be seen from the results of the images of FIG. 3A, green fluorescence was not observed in the cortex and hippocampal tissues in the case of the control group injected with only GFP without the peptide, whereas when the cell-penetrating peptide-GFP was injected, it was confirmed that green fluorescence was clearly observed in the cerebral cortex and hippocampal tissues compared with the control group. Even through the quantitative results of FIG. 3B, it was confirmed that when the cell-penetrating peptide-GFP was injected, fluorescence was detected to be higher in the cerebral cortex by about 2.2 times (p=0.009) and by about 1.78 times in the hippocampus (p=0.009) than when only GFP was injected. Through these results, it was confirmed that the cell-penetrating peptide according to the present disclosure has excellent cell-permeability even in vivo, and the cell-penetrating peptide was found to effectively deliver cargo into the cell as a substance deliverer.

Example 6. Comparison of Effects with Cell-Penetrating Peptides in the Art

The present inventors tried to compare degrees of cell permeability of a cell-penetrating peptide known in the art and 12 cell-penetrating peptides according to the present disclosure. To this end, cell permeability analysis experiments by using flow cytometry, and in vivo blood-brain barrier (BBB) permeability analysis experiments were each performed as follows, and angiopep-2 was used as the known cell-penetrating peptide. An angiopep-2 peptide consists of 19 amino acid residues, and is known to enter the cell by binding to a low-density lipoprotein receptor-related protein-1 (LRP-1), a receptor expressed in the BBB.

6-1. Comparative Analysis of Cell Permeation Effect through Flow Cytometry

First, with respect to the transpep-1-FITC and angiopep-2-FITC prepared in Example 1-2, an amount of fluorescence inflow into a single cell was identified and quantified through flow cytometry. Specifically, an hCMEC/D3 cell line was aliquoted at 15,000 cells/well using an EGM culture medium containing 2% bovine calf serum (BCS), and 24 hours later, cells were treated with each of the two peptides at a concentration of 10 μM, and then were incubated for 2 hours at 37° C., under $CO_2$ conditions. Thereafter, the cells were washed with 1×PBS, and then were separated from the bottom of the plate by incubating for 3 minutes after 1.1% trypsinase-EDTA (TE) was added, and then an EGM cell culture solution of about 3 times the amount of TE was added, and the sample was centrifuged at 100 rpm for 5 minutes. Next, the supernatant was removed by suction, and the cells were resuspended in 250 μl of 1×PBS, and then transferred to a BD Falcon 12×75 mm Tube with Cell Strainer Cap, and inflow of fluorescence according to each peptide was analyzed by flow cytometry.

Figure 4:
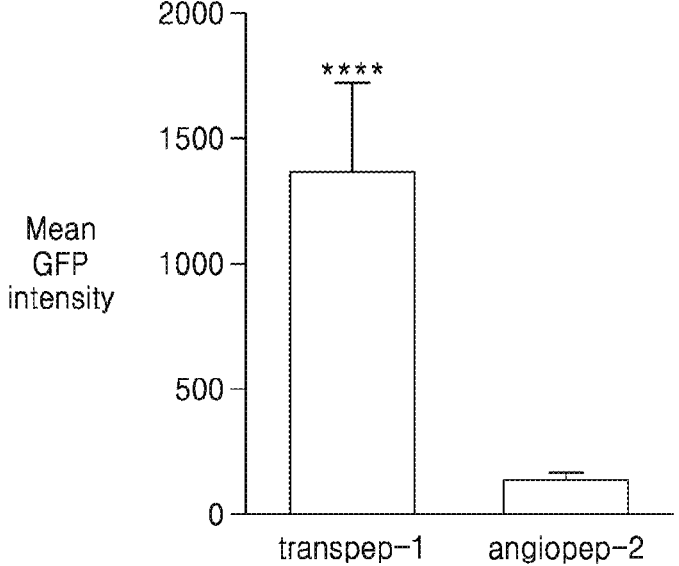
FIG. 4 shows results of a comparative analysis of cell permeability of angiopep-2, a cell-penetrating peptide known in the art, and transpap-1 according to the present disclosure, through flow cytometry using transpep-1-FITC and angiopep-2-FITC.
Figure 5A:
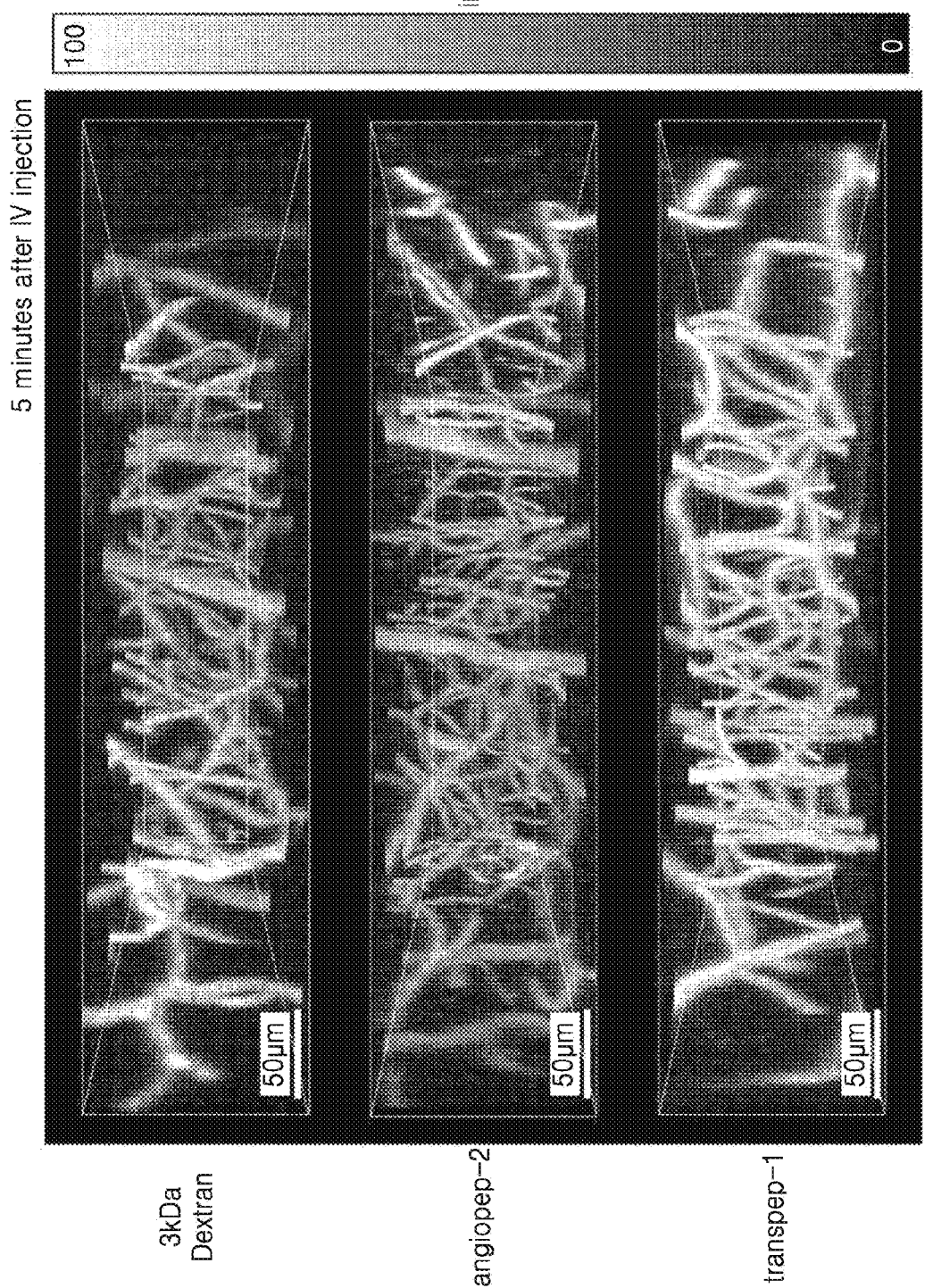
FIG. 5A shows results of analyzing in vivo blood-brain barrier (BBB) permeability by using a two-photon microscope, 5 minutes after intravenous administration of transpep-1-FITC and angiopep-2-FITC to mice, in order to compare and analyze BBB permeability of angiopep-2 and transpap-1 according to the present disclosure.
Figure 5B:
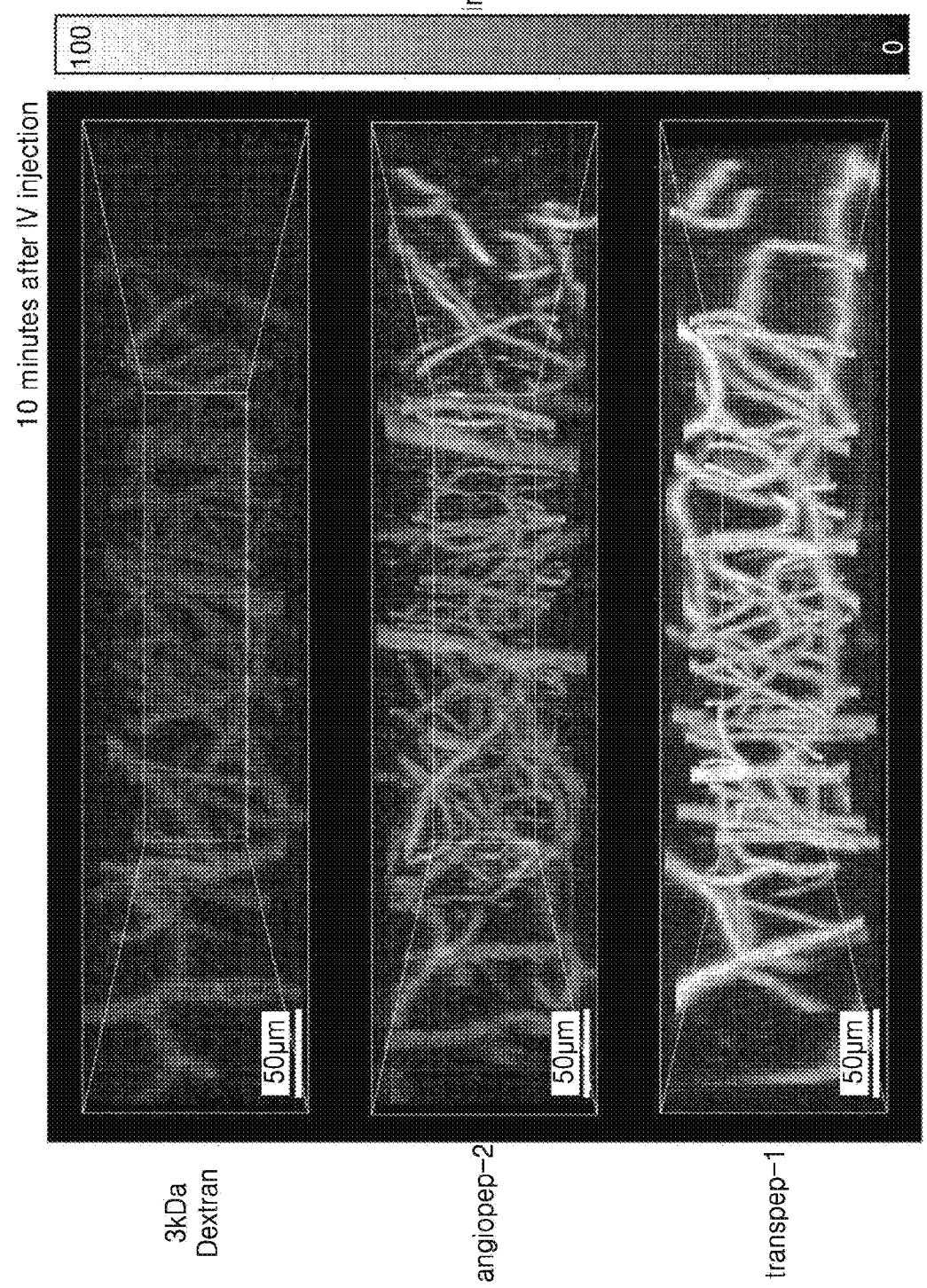
FIG. 5B shows results of analyzing in vivo BBB permeability by using a two-photon microscope, 10 minutes after intravenous administration of transpep-1-FITC and angiopep-2-FITC to mice, as in FIG. 5A.
Figure 5C:
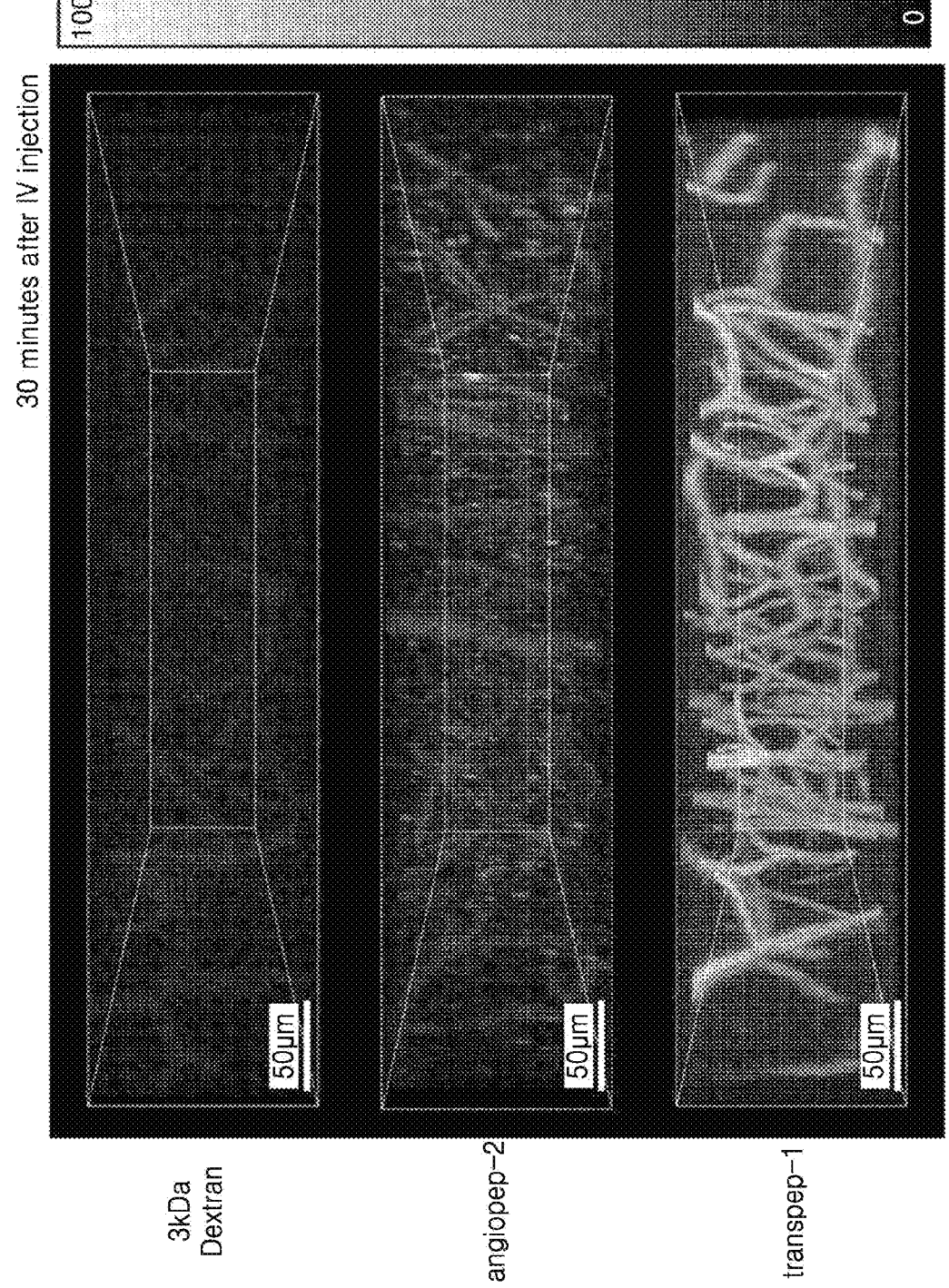
FIG. 5C shows results of analyzing in vivo BBB permeability by using a two-photon microscope, 30 minutes after intravenous administration of transpep-1-FITC and angiopep-2-FITC to mice as in FIG. 5A.
Figure 5D:
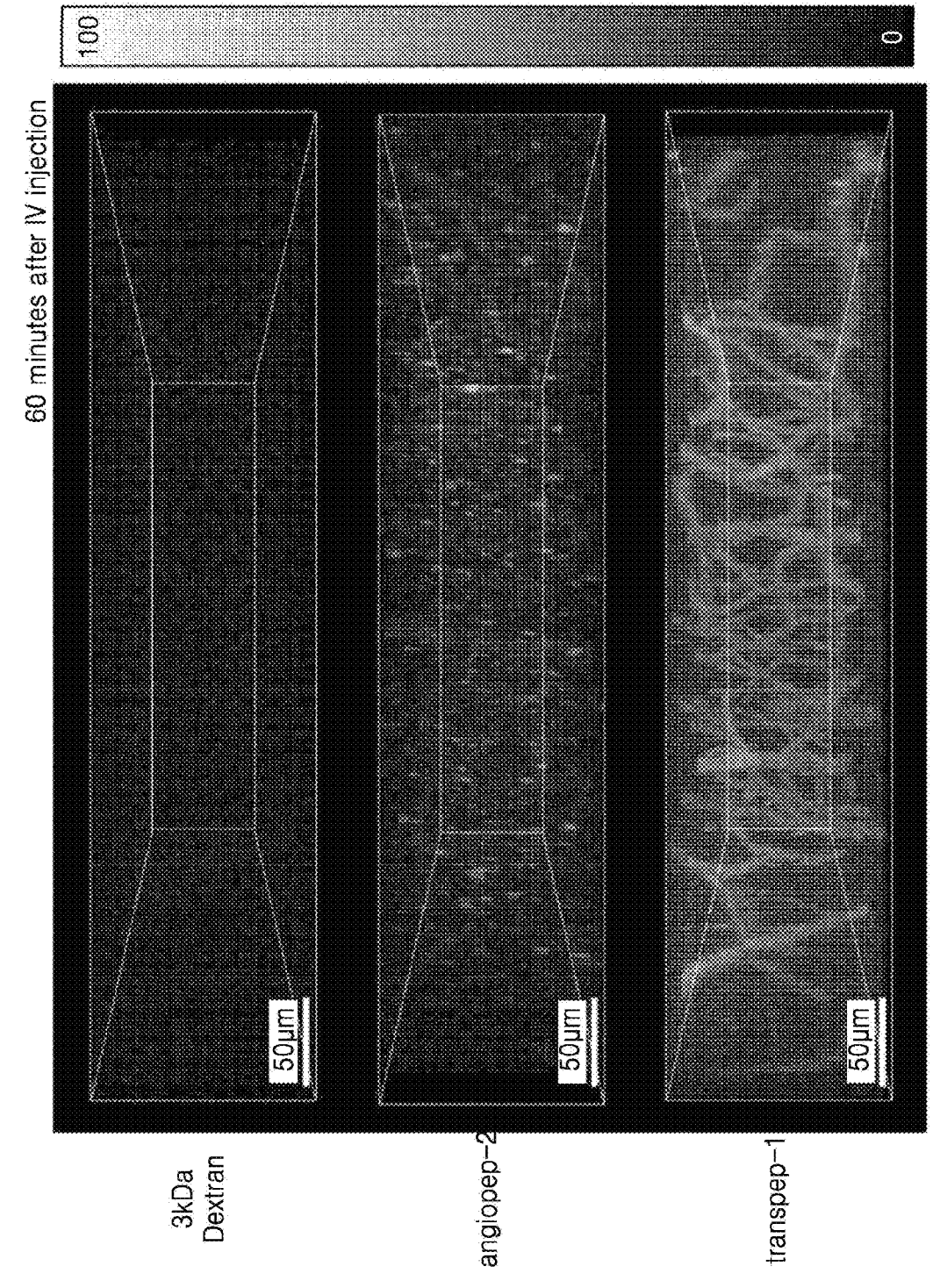
FIG. 5D shows results of analyzing in vivo BBB permeability by using a two-photon microscope, 60 minutes after intravenous administration of transpep-1-FITC and angiopep-2-FITC to mice as in FIG. 5A.
Figure 5E:
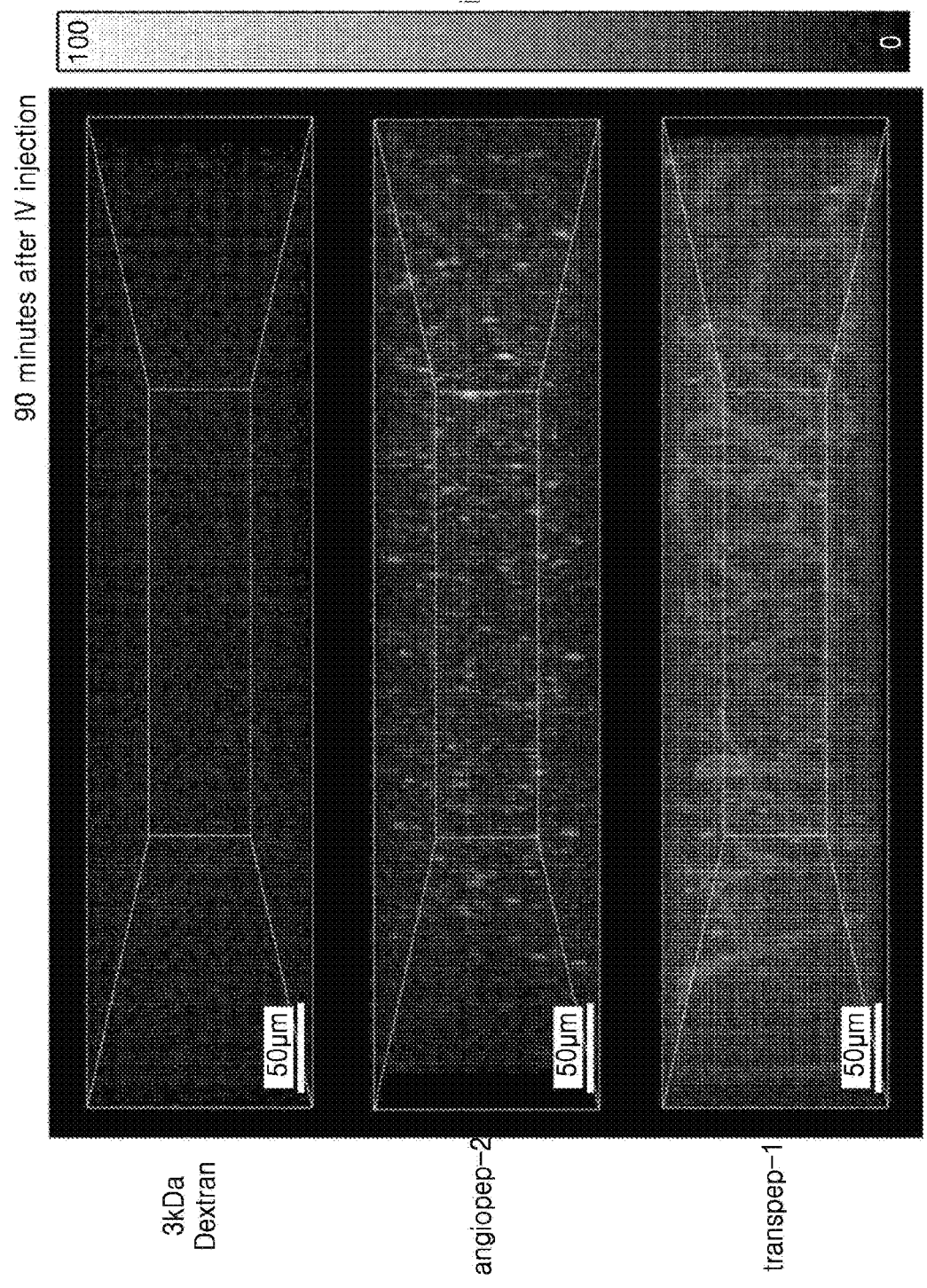
FIG. 5E shows results of analyzing in vivo BBB permeability by using a two-photon microscope, 90 minutes after intravenous administration of transpep-1-FITC and angiopep-2-FITC to mice as in FIG. 5A.
Figure 5F:
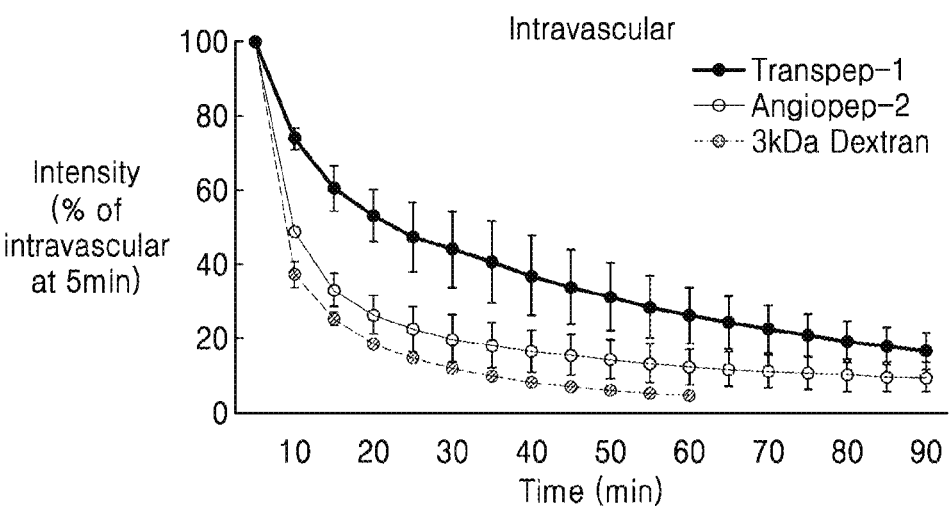
FIG. 5F shows results of quantifying the results of imaging of FIGS. 5A to 5E.
Figure 5F:
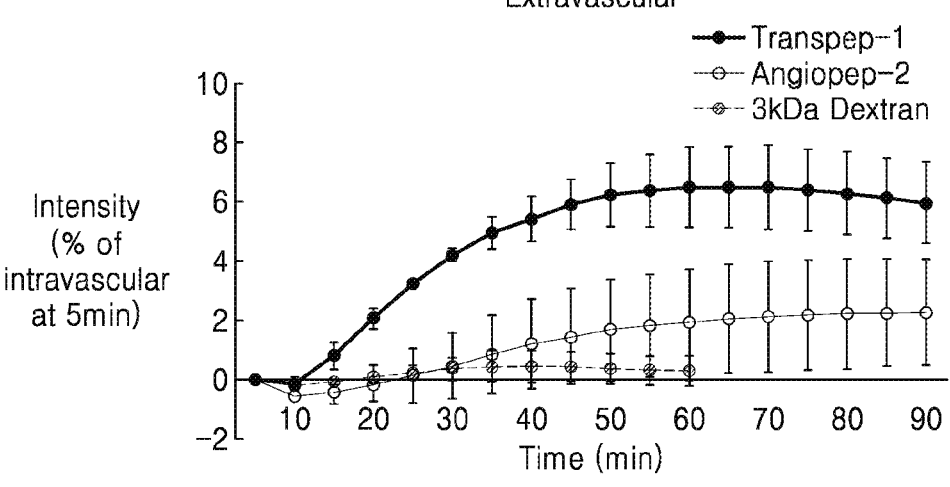

As a result, as shown in FIG. 4, the fluorescence intensity was shown to be significantly higher (p<0.0001) when transpep-1 peptides were treated, compared to when angio-pep-2-FITC peptides were treated. Through this, it was confirmed that the transpep-1 peptide according to the present disclosure has significantly higher cell permeability than the angiopep-2 peptide.

6-2. Comparative Analysis of In Vivo Blood-Brain Barrier (BBB) Permeability

Next, in order to compare in vivo BBB permeability of transpep-1 according to the present disclosure and angiopep-2, an experiment was conducted as follows.

Specifically, in order to perform in vivo real-time imaging using a two photon microscopy, operations to install a cranial window were performed in living mice (C57BL/6). Before making the cranial window, inhalation anesthesia was induced with 3% isoflurane in the mice, and the body temperature of the mice was maintained at 36.5° C. to 37.5° C. by using a heating pad. After induction of anesthesia, the concentration of isoflurane was adjusted to 1.5% to maintain anesthesia. In addition, to confirm the degree of maintenance of anesthesia, heart rate and $SpO_2$ were confirmed in real time. Afterwards, craniotomy was performed by using a dental drill in order that the cranial window has a diameter of 3 mm at the skull coordinates of ML, +2.5 mm, and AP, −1.5 mm. After the skull was removed by craniotomy, the brain was covered with a cover glass having a diameter of 4 mm, and the cover glass was adhered by using a cyano-acrylic bond. Next, a head frame, capable of fixing the mouse's head under a two-photon microscope, was attached so that the cover glass would come to the center. After a first bonding of the cover glass and the frame by using the bond, a second bonding was performed and all exposed skulls were covered from the border of the cover glass with dental resin so that imaging could be performed by using a water immersion lens. After surgery, 5 mg/kg of enrofloxacin and meloxicam were injected to relieve inflammation caused by surgery.

After cranial window surgeries were performed according to the above procedure, there was a recovery period of 4 weeks to 6 weeks, and then the cranial windows were wiped with secondary distilled water and 70% alcohol, and the suspended matter was removed, in order that during an experiment, only pure distilled water would exist between the lens and the coverglass. Subsequently, the mice were anesthetized with 2% isoflurane, and then transferred to a stereotaxic frame to fix the head frame, anesthesia was maintained with 1.5% isoflurane, body temperature was maintained at 36.5° C. to 37.5° C., and then a tube was connected to the tail vein and fixed. To use a water immersion lens (25×, NA: 0.9), the cleaned cranial windows were filled with distilled water, focused, and dextran conjugated with 70 kDa Texas red was inserted through the tail vein tube, at a dose of 1.5 ml/kg (body weight, concentration: 5% (w/v)).

Then, the imaging range (FOV) was set in order that the pial artery, penetrating arteriole, venule, and pial vein could all be included, and vasculature imaging (1) was performed. As described above, the vasculature imaging (1) was performed at a depth of about 350 μm to 400 μm including the pial vessel. Next, for in vivo real-time imaging (2), the image parameters were adjusted so that the visual resolution was 1 minute, and a range of 354 μm×354 μm was imaged at a resolution of 512×512. 75 sheets at a z-axis resolution of 2 μm were obtained, that is, a thickness of 150 μm was set to be in a depth range of 50 μm to 200 μm excluding the pial vessel. After setting up for performing an in vivo real-time imaging (2), 15 mg/kg of transpep1-FITC or angioopep-2-FITC was injected through the tail vein tube, and then imaging was proceeded for 90 minutes using the same image parameters as the setting above.

After reconstructing the vasculature images (1) obtained from the two-photon microscope through the above-mentioned method and the in vivo real-time images (2) into a three-dimensional matrix, in vivo real-time imaging matrices were registered to the vasculature imaging matrix. The registration method uses linear registration in principle, and a rigid body and a similarity parameter were selectively used according to movement artifacts at times the images were acquired. Among the registered real-time imaging matrices, the region inside a blood vessel binarized by using 70 kDa-Texas red-dextran was defined as an intravascular region, and the external region was defined as an extravascular region.

Binarization may be performed by using imageJ and matlab. In case of imageJ, CLAHE (local contrast enhanced thresholding) was used, and in case of matlab, an algorithm using Mexican hat, otsu, and local contrast was used. After determining the internal and external regions of the blood vessel, the coordinates were applied to the coordinates of the real-time imaging matrix to observe changes in transpep1-FITC or angiopep-2-FITC in the intravascular/extravascular region.

In addition, in order to quantify the results observed by the imaging, an average value of the first measured intensity in the intravascular region was set to be 100%, and the average value of the first intensity in the extravascular region set to be 0%, and by normalizing voxel values of the matrices present on all visible regions, the percentage was mapped in an in vivo real-time imaging matrix. Normalized intensity values were derived according to the following equation. In this regard, in the following equation, "averaged Intra Intensity0" is the average value of the first intensity in the intravascular region, and "averaged extra Intensity0" is the average value of the first intensity in the extravascular region.

$$\text{Normalized Intensity } (x, y, z, t) =$$

$$\frac{\text{Intensity } (x, y, z, t) - \text{averaged extra intensity0}}{\text{averaged intra intensity0} - \text{averaged extra intensity0}} \times 100$$

As a result of the experiment, as shown in FIGS. 5A to 5F, when transpep-1-FITC was injected, it was confirmed that fluorescence was observed at a higher level in the intravascular region longer than when angiopep-2-FITC was injected, resulting in higher in vivo stability. In addition, it was confirmed that when transpep-1-FITC was injected, an amount delivered to the extravascular area was greater than when angioopep-2-FITC was injected. In conclusion, it was confirmed that transpep-1 according to the present disclosure has superior in vivo stability and delivery efficiency than a angiopep-2 peptide.

The above description of the present disclosure is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

INDUSTRIAL APPLICABILITY

Since the novel cell-penetrating peptide according to the present disclosure has excellent cell permeability and an excellent substance delivery effect, the novel cell-penetrating peptide is expected to be useful in the field of research, and in the field of diagnosis or treatment of various diseases, by effectively delivering substances having various biological activities into the living body, such as cells and tissues.

---

The invention claimed is:

1. An in vivo method of substance delivery, comprising treating cells with a complex comprising a cell-penetrating peptide and a biologically active material conjugated to a terminal of the cell-penetrating peptide, wherein the cell-penetrating peptide consists of any one amino acid sequence selected from the group consisting of SEQ ID NOs: 1 to 12.

2. The in vivo method of substance delivery of claim 1, wherein the cell is any one selected from the group consisting of brain endothelial cells, cancer cells, blood cells, lymphocytes, immune cells, stem cells, induced pluripotent stem cells (iPSCs), neural stem cells (NSCs), T cells, B cells, natural killer cells (NK cells), macrophages, microglia, neurons, astrocytes, and muscle cells.

* * * * *

SEQUENCE LISTING

```
<160> NUMBER OF SEQ ID NOS: 12

<210> SEQ ID NO 1
<211> LENGTH: 16
<212> TYPE: PRT
<213> ORGANISM: Artificial Sequence
<220> FEATURE:
<223> OTHER INFORMATION: transpep-1

<400> SEQUENCE: 1

Gly His His Glu Arg Leu Lys Ser Asp Glu Trp Ser Val Thr Ser Gly
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: transpep-2

<400> SEQUENCE: 2

Gly His His Glu Arg Leu Lys Ser Ala Glu Trp Ser Val Thr Ser Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: transpep-3

<400> SEQUENCE: 3

Gly His His Glu Arg Leu Lys Ser Asp Ala Trp Ser Val Thr Ser Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: transpep-4

<400> SEQUENCE: 4

Gly His His Glu Arg Leu Lys Ser Asp Glu Trp Ala Val Thr Ser Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: transpep-5

<400> SEQUENCE: 5

Gly His His Glu Arg Leu Lys Ser Ala Ala Trp Ser Val Thr Ser Gly
1               5                   10                  15
```

```
<210> SEQ ID NO 6
<211> LENGTH: 16
<212> TYPE: PRT
<213> ORGANISM: Artificial Sequence
<220> FEATURE:
<223> OTHER INFORMATION: transpep-6

<400> SEQUENCE: 6

Gly His His Glu Arg Leu Lys Ser Ala Glu Trp Ala Val Thr Ser Gly
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: transpep-7

<400> SEQUENCE: 7

Gly His His Glu Arg Leu Lys Ser Asp Ala Trp Ala Val Thr Ser Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: transpep-8

<400> SEQUENCE: 8

Gly His His Glu Arg Leu Lys Ser Glu Glu Trp Ser Val Thr Ser Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: transpep-9

<400> SEQUENCE: 9

Gly His His Glu Arg Leu Lys Ser Tyr Glu Trp Ser Val Thr Ser Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: transpep-10

<400> SEQUENCE: 10

Gly His His Glu Arg Leu Lys Ser Asp Asp Trp Ser Val Thr Ser Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: transpep-11

<400> SEQUENCE: 11

Gly His His Glu Arg Leu Lys Ser Asp Tyr Trp Ser Val Thr Ser Gly
1               5                   10                  15
```

```
<210> SEQ ID NO 12
<211> LENGTH: 16
<212> TYPE: PRT
<213> ORGANISM: Artificial Sequence
<220> FEATURE:
<223> OTHER INFORMATION: transpep-12

<400> SEQUENCE: 12

Gly His His Glu Arg Leu Lys Ser Asp Glu Trp Asn Val Thr Ser Gly
1               5                   10                  15
```